United States Patent [19]

Bernier et al.

[11] Patent Number: 5,061,489

[45] Date of Patent: Oct. 29, 1991

[54] INSECTICIDAL BACILLUS THURINGIENSIS STRAINS WITH ACTIVITY AGAINST LEPIDOPTERA

[75] Inventors: Roger L. Bernier, Burlington, Canada; Martyn D. Collins, Midhurst, England; Ann L. Gray, Oakville, Canada

[73] Assignee: Imperial Chemical Industries PLC, London, England

[21] Appl. No.: 290,490

[22] Filed: Dec. 27, 1988

[30] Foreign Application Priority Data

Dec. 24, 1987 [GB] United Kingdom ................. 8730132
Dec. 24, 1987 [GB] United Kingdom ................. 8730133

[51] Int. Cl.⁵ .......................... A01N 63/00; C12N 1/20
[52] U.S. Cl. .................................... 424/93; 435/71.2; 435/252.5; 435/832

[58] Field of Search ....................... 435/69.1, 71.2, 91, 435/172.1, 172.3, 170, 252.5, 320, 832, 69, 22, 59, 64, 66; 424/93; 536/27

[56] References Cited

PUBLICATIONS

Ignoffo et al., 1982, *Journal of Invertebrate Pathology*, 39:244–246.
Vaeck et al., 1987 (Jul.), *Nature*, 328:33–37.

*Primary Examiner*—Richard A. Schwartz
*Assistant Examiner*—Richard C. Peet
*Attorney, Agent, or Firm*—Cushman, Darby & Cushman

[57] ABSTRACT

The newly discovered strains A20 and A29 of *Bacillus thuringiensis*, useful as sources of insecticidal endotoxin; and the application thereof to plants to combat insect infestations.

9 Claims, No Drawings

INSECTICIDAL BACILLUS THURINGIENSIS STRAINS WITH ACTIVITY AGAINST LEPIDOPTERA

The present invention relates to novel bacterial strains, and in particular to novel strains of the bacterium *Bacillus thuringiensis* and uses therefor.

The organism *Bacillus thuringiensis* produces a protein crystal endotoxin which kills insects. It is not however toxic to mammals. It is thus very useful as an agricultural insecticide, in particular against *Lepidoptera*, and strains of *Bacillus thuringiensis* have been used as agricultural insecticides for a number of years.

The strain of *Bacillus thuringiensis* which is most commonly used commercially is HD-1 (available from the collection of *Bacillus thuringiensis* strains maintained by the U.S. Department of Agriculture). We have now discovered novel strains of *Bacillus thuringiensis* having generally similar properties to HD-1, but distinguished therefrom by improved insecticidal activity against a range of lepidopteran pests.

According to the present invention we provide the novel strains A20 and A29 of *Bacillus thuringiensis*, deposited on Oct. 20, 1987 at the National Collection of Industrial and Marine Bacteria (Torry Research Station, P.O. Box 31, 135 Abbey Rd., Aberdeen, AB9 8DG, United Kingdom) under the accession numbers NCIB 12570 and NCIB 12571, respectively. We further provide novel insecticidal compositions characterised in that they contain a δ-endotoxin produced by said strains A20 or A29, and a method of protecting plants from insect attack which comprises exposing the insects to a δ-endotoxin produced by said strains A20 or A29.

The strain A20 was isolated from soil found under a cedar tree in Coburg, Ontario. The strain A29 was isolated from a colorado potato beetle larva. In morphology and general biochemical properties they are both generally similar to HD-1. The morphology of the strains is compared in Table 1.

TABLE 1
MORPHOLOGY

| Strain | Crystals | Cell Morphology | Colony Morphology |
|---|---|---|---|
| HD-1 | Medium bi-pyramids, plus undefined shaped crystals | Rods in pairs with terminal spores which do not distend the cell | Lecithinase negative, round colonies; umbonate, yellow centres; 1.0 cm diameter |
| A20 | Medium to large bipyramids and rounded pyramids | Rods in pairs and short chains; subterminal to terminal non-distending spores | Lecithinase negative; teardrop shape; umbonate; yellow centre; 1.0 cm × 0.8 cm |
| A29 | Medium bi-pyramids | Rods in short chains: terminal non-distending spores | Lecithinase positive; round to teardrop shape colonies; umbonate; yellow centre; 1.0 cm × 0.9 cm |

Biochemical properties of the strains are compared in Tables 2–4.

TABLE 2
Biochemical Markers on Microtitre Plate

| Reagent | HD-1 | A20 | A29 |
|---|---|---|---|
| MR | + | + | + |
| VP | + | − | + |
| Starch | + | + | + |
| DNAse | − | − | − |
| Urease | + | + | + |
| Mannose | − | − | − |
| Sucrose | − | − | − |
| Cellobiose | − | − | − |
| Glucose | + | + | + |
| Maltose | + | + | (+) |
| Salicin | + | + | + |
| Thorneleys | + | (+) | + |

−: Negative Reaction;
+: Postive Reaction;
(+): Partial Reaction

TABLE 3
Biochemical Markers on ID-IDENT Plates

| | HD-1 | A20 | A29 |
|---|---|---|---|
| Indole production | − | − | − |
| N-acetyl-glucosaminidase | − | − | − |
| α-glucosidase | − | * | − |
| α-arabinosidase | − | − | − |
| β-glucosidase | − | * | − |
| α-fucosidase | − | − | − |
| phosphatase | − | − | − |
| α-galactosidase | − | − | − |
| β-galactosidase | − | − | − |
| Inoxyl acetate | + | + | + |
| Use of arginine | − | − | − |
| Leucine aminopeptidase | − | − | − |
| Proline aminopeptidase | − | − | − |
| Pyroglutamic acid arylamidase | − | + | − |
| Tyrosine aminopeptidase | − | − | − |
| Arginine aminopeptidase | + | + | + |
| Alanine aminopeptidase | − | − | − |
| Histidine aminopeptidase | − | − | − |
| Phenylalanine aminopeptidase | − | − | − |
| Glycine | − | − | − |
| Catalase | + | + | + |

*partial color change (hard to read).
"ID-IDENT" is a Trade Mark of Api Analytab Products

TABLE 4
Biochemical Markers on API-ZYME Plates

| | HD-1 | A20 | A29 |
|---|---|---|---|
| Control | 0 | 0 | 0 |
| Alkaline phosphatase | 0 | 0 | 0 |
| Esterase (C-4) | 0 | 0 | 0 |
| Esterase Lipase (C-8) | 0 | 0 | 0− |
| Esterase Lipase (C-14) | 0 | 0 | 0 |
| Leucine aminopeptidase | + | + | + |
| Valine aminopeptidase | 0 | 0 | 0 |
| Cysteine aminopeptidase | 0 | 0 | 0 |
| Trypsin aminopeptidase | 0 | 0 | 0 |
| Chymotrypsin | 0 | 0 | 0 |
| Acid phosphatase | 0 | 0 | + |
| Phosphoamidase | 0 | 0–1 | 0 |
| α-galactosidase | 0 | 0 | 0 |
| β-galactosidase | 0 | 0 | 0 |
| β-glucusuronidase | 0 | 0 | 0 |
| α-glucosidase | 0 | 0 | 0 |
| β-glucosidase | 0 | 0 | 0 |
| η-acetyl-β-glucosaminidase | 0 | 0 | 0 |
| α-mannosidase | 0 | 0 | 0 |
| α-fucosidase | 0 | 0 | 0 |

API-ZYME is a Trade Mark of API ANALYTAB PRODUCTS
0 = no reaction
+ = positive reaction In view of these similarities, it is surprising that A20 and A29 show significantly improved insecticidal activity over a range of lepidopteran pests as compared with HD-1.

The strains according to the invention may be prepared in any quantity required by fermenting a sample of NCIB 12570 or NCIB 12571 obtained from the National Collection of Industrial and Marine Bacteria under suitable conditions in an appropriate medium. Such conditions and media are well known to the art. The media will, for example, generally contain a nitrogen source (e.g. fish protein) and a carbohydrate source such as starch. Suitable conditions include a temperature in the range 15°–45° C., and an approximately neutral pH. Fermentation most conveniently carried out in batches, typically for periods of 1-3 days.

Insecticidal compositions according to the invention may be obtained from the fermentation liquor by concentration, for example by centrifugation or filtration followed by addition of any desired and appropriate formulating agents. Formulating agents which may be useful include for example surface active agents, e.g., wetting agents: solid diluents, dispersing agents and UV stabilisers. If desired, solid formulations may be prepared by known methods.

The process of the invention is generally carried out by spraying on to plants infested with or liable to infestation by insects insecticidal compositions as described above diluted with a diluent such as water. The insecticidal agent is the toxic endotoxin: if desired this may be applied to the plants or insects infesting them independently of the bacteria that produce it, but separation of the crystalliferous protein from the bacteria is generally not necessary.

One method of carrying out the process of the invention is to arrange for the plant susceptible to insect attack to produce the δ-endotoxin in situ. This is done by cloning a δ-endotoxin gene from either of the strains NCIMB 12570 or 12571, by known methods, providing it with a suitable promoter (for example the CaMV35S promoter) which will cause expression of the gene in plants, and transforming the plant by known methods (e.g., the use of Ti plasmids). Such processes are described in more detail in EPA 142924 (Agrigenetics), the disclosure of which incorporated herein by reference.

Insects which are most effectively combatted by the process of the invention are lepidoptera, for example, those in Table 5 below.

TABLE 5

| Common Name | Latin Name |
| --- | --- |
| Spruce budworm | *Choristoneura fumiferana* |
| Gypsy moth | *Lymantria dispar* |
| Cabbage looper | *Trichoplusia ni* |
| Corn earworm | *Heliothis zea* |
| Beet armyworm | *Spodoptera exiqua* |
| Diamondback moth | *Plutella xylostella* |
| European Corn borer | *Ostrinia nubilalis* |

The process of the invention may be used to protect a wide variety of plants prone to infestation by lepidoptera. Specific examples of commercially important plants to be protected by the invention are maize (corn) and conifers: as well as rice, small grain cereals such as wheat and barley, and vegetables including lettuce, tomatoes and sugar beet.

The following Examples illustrate the invention.

EXAMPLE 1

Isolation of the BT strain A20 according to the invention

The soil sample found under a cedar tree in Coburg, Ontario was diluted by placing 0.5 g of the sample into a dilution bottle containing 45 ml of 0.05% peptone to give a $10^{-1}$ dilution. The sample was then heat treated by transferring it to a 60° C. water bath for 10 minutes. Sequential dilutions were made by taking 0.5 ml of the sample with the highest dilution and placing it into 4.5 ml of 0.05% peptone (e.g. 0.5 ml of the $10^{-1}$ dilution into 4.5 ml peptone diluent gives a $10^{-2}$ dilution); this was repeated until a $10^{-5}$ dilution was obtained. *B.cereus* selective medium (*Bacillus cereus* Agar base, Code CM617 from Oxoid, Canada) and esculin agar (in g/L of water: esculin 1.0; ferric citrate 0.5; peptone 10; NaCl 5; Agar 20) were used to plate $10^{-3}$ to $10^{-6}$ dilutions. The plated samples were incubated at 30° C. for 5 days and then examined for potential B.t. colonies. Slides were made of the chosen colonies using the Smirnoff staining procedure and were examined under the microscope (at a magnification of 1000x using the oil immersion lens) for the presence of darkly staining parasporal crystals which were usually but not necessarily bipyramidal in shape. Crystal-positive colonies were streaked onto nutrient agar in order to ensure a pure culture, and incubated for another 5 days at 30° C. The Smirnoff staining procedure was repeated to confirm crystal presence, and to check for purity. Purified colonies were transferred to nutrient agar slants and stored in a refrigerator at 40° C. for further use.

EXAMPLE 2

Isolation of the BT strain A29 according to the invention

The source of the A29 strain was a dead Colorado Potato Beetle Larva. The insect was ground in a sterilised mortar and a pestle with a small amount of the peptone diluent. The liquid was recovered using a pasteur pipette, and placed into a test tube containing 4.5 ml of the peptone diluent (0.05% peptone in water), this was considered a $10^{-1}$ dilution. The sample was then heat treated by transferring it to a 60° C. water bath for 10 minutes. Sequential dilutions were made by taking 0.5 ml of the sample with the highest dilution and placing it into 4.5 ml of 0.05% peptone (e.g., 0.5 ml of the $10^{-1}$ dilution into 4.5 ml peptone diluent gives a $10^{-2}$ dilution); this was repeated until a $10^{-5}$ dilution was obtained. *B. cereus* selective medium (*Bacillus cereus* agar base, Code CM617 from Oxoid, Canada) and esculin agar (in g/l of water: esculin 1.0; ferric citrate 0.5; peptone 10; NaCl 5; Agar 20) were used to plate $10^{-3}$ to $10^{-6}$ dilutions. The plated samples were incubated at 30° C. for 5 days and then examined for potential Bt colonies. Slides were made of the chosen colonies using the Smirnoff staining procedure and were examined under the microscope (at a magnification of 1000x using the oil immersion lens) for the presence of darkly staining parasporal crystal which was usually but not necessarily bipyramidal in shape. Crystal-positive colonies were streaked into nutrient agar in order to ensure a pure culture, and incubated for another 5 days at 30° C. The Smirnoff staining procedure was repeated to confirm crystal presence, and to check for purity. Purified colonies were transferred to nutrient agar slants and stored in a refrigerator at 4° C. for further use.

EXAMPLE 3

Propagation of the BT strains according to the invention

Inoculum of A20 was transferred from a slant to a 250 ml Erlenmeyer flask containing 100 ml of CRL No. 1 medium (in g or ml/liter of water: nutrient broth 8; glucose 6; yeast extract 5; xylose 0.5; cotton seed flour extract 30 ml; corn steep liquor 3.2 ml; Mary Mendel's salt mixture 1 ml) and incubated with agitation at 30° C. and 300 rpm. After 24 hours, the entire 100 ml was used to inoculate 1 liter of the same medium in a 2L flask; this was incubated with agitation for 5 days at 300 rpm at 30° C.

A29 was propagated in an identical manner.

EXAMPLE 4

Formulation according to the invention

Upon completion of the fermentation cycle, A20 bacteria was harvested by first separating the B.t. spores and crystals from the fermentation broth by centrifugation or microfiltration. The recovered spores and crystals were resuspended in 100 ml of water and formulated into a liquid concentrate by adding 4.9 g of Morwet D-425 (dispersing agent), 4.9 g of Veegum HV (suspending agent), 4.9 ml of Tween 80 (wetting agent) and 24.4 ml of Sorbo (anti-freezing agent). Each ingredient as added separately in order stated above. The product was kept at 40° C. prior to use. A similar formulation was made up using A29, and also HD-1; the latter was used as a control.

EXAMPLE 5

Efficacy of the BT strain A20 and A29 in protecting plants from insect attack Using the formulations described in Example 4, A20 and A29 B.t. strain spores and crystals mixtures, obtained as described in Example 3, were tested against Spruce budworm in a foliage assay. Branches of fir-tree naturally infested with the insect (4-5th instar larvae) were sprayed using a backpack sprayer model MRY-2 (from Hartvig Jensen & Co., Denmark). For A20 and HD-1, the size of the drops (in diameter) were ranging from 20 to 120 um for an average of 32 $\mu$m. For A29 the drop diameter ranged from 20 to 60 $\mu$m for an average of 30 um. In all cases there were approximately 11 drops per needle. All strains were sprayed at a concentration of $30 \times 10^9$ IU/hectare. The treated branches were incubated in a growth chamber until pupation. The results were expressed by the percentage of mortality ([number of dead insects/number of dead insects+number of living insects] $\times 100$).

| STRAIN | % MORTALITY | POTENCY RATIO* |
|---|---|---|
| HD-1 | 47 | 1.7 |
| A20 | 60 | 8.7 |
| A29 | 65 | 6.0 |

*mortality divided by the amount of B.t. powder (in gramme) used in the formulation.

In this example, A20 was 5.1×more active, and A29 3.53×more active than HD-1, based on their potency ratios.

EXAMPLE 6

Further tests of the toxicity of A20 and A29 to insect pests

After the 5 day incubation carried out in Example 3, the cells, spores and crystals were harvested by centrifugation and acetone-precipitated. The resulting powder was incorporated into an artificial diet suitable for the tested insect. The diet was fed to the insects and mortality recorded using standard methodology. Comparative tests were carried out using HD-1.

| INSECT | STRAIN | LC50* | POTENCY+ INCREASE |
|---|---|---|---|
| *Trichoplusia ni* | A20 | 0.9 | 6.3 |
|  | A29 | 2.9 | 1.97 |
| (4 day-old larvae on diet) | HD1 | 5.7 | 1 |
| *Plutella xylostella* | A20 | 0.43 | 9.3 |
|  | A29 | 1.78 | 2.24 |
| (4 day-old larvae on diet) | HD1 | 4.00 | 1 |
| *Heliothis zea* | A20 | 19.7 | 2.7 |
|  | A29 | 27.6 | 1.92 |
| (1st instar larvae on diet) | HD1 | 52.9 | 1 |

*LC50 in ug of solid content per ml of diet.
*+Ratio of LC50 to LC50 of control

We claim:

1. The biologically isolated strains A20 and A29 of *Bacillus thuringiensis*, deposited at the National Collection of Industrial and Marine Bacteria Scotland under the reference numbers NCIB 12570 and 12571, respectively.

2. An insecticidal formulation for combatting *Lepidoptera* species which comprises as active ingredient an insecticidal δ-endotoxin produced by one of the strains A20 and A29.

3. An insecticidal formulation as claimed in claim 2 which further comprises a solid diluent or a surface active agent.

4. A process of protecting plants against attack by insects of the order *Lepidoptera* which comprises exposing such attacking insects to the δ-endotoxin produced by one of the strains claimed in claim 1.

5. A process as claimed in claim 4 which comprises spraying the plants prior to or during such attack with insecticidally effective amounts of a formulation claimed in either of claims 2 or 3.

6. A process as claimed in any of claims 4 to 5 in which the plant is maize (corn) or a conifer.

7. A process as claimed in claim 6 in which the insect is Spruce Budworm or Gypsy Moth.

8. A process as claimed in claim 6 in which the insect is Corn Earworm or European Corn Borer.

9. A process as claimed in any of claims 4-8 in which the δ-endotoxin is derived from A20.

* * * * *